United States Patent [19]

Seibert et al.

[11] 4,411,887

[45] Oct. 25, 1983

[54] USE OF ALKYLENE OXIDE COPOLYMERS AS EMOLLIENTS IN COSMETIC PREPARATIONS

[75] Inventors: Karl Seibert, Duren; Heinz Praetorius, Lendersdorf; Gunter Poppel, Duren-Niederau, all of Fed. Rep. of Germany

[73] Assignee: Akzona Incorporated, Asheville, N.C.

[21] Appl. No.: 296,688

[22] Filed: Aug. 27, 1981

Related U.S. Application Data

[63] Continuation of Ser. No. 37,980, May 11, 1979, abandoned.

[30] Foreign Application Priority Data

May 18, 1978 [DE] Fed. Rep. of Germany ....... 2821654

[51] Int. Cl.³ ............................................. A61K 31/74
[52] U.S. Cl. .................................................... 424/78
[58] Field of Search ......................................... 424/78

[56] References Cited

U.S. PATENT DOCUMENTS

| | | | |
|---|---|---|---|
| 3,029,216 | 4/1962 | Bailey | 260/42 |
| 3,740,421 | 6/1973 | Schmolka | 424/65 |
| 3,867,533 | 2/1975 | Schmolka | 424/258 |
| 4,057,622 | 11/1977 | Hase et al. | 424/78 |
| 4,129,717 | 12/1978 | Praetorius et al. | 525/187 |

FOREIGN PATENT DOCUMENTS

| | | |
|---|---|---|
| 1617480 | 4/1972 | Fed. Rep. of Germany . |
| 2535777 | 2/1976 | Fed. Rep. of Germany . |
| 1093672 | 12/1967 | United Kingdom . |
| 1173743 | 12/1969 | United Kingdom . |
| 1214975 | 12/1970 | United Kingdom . |
| 1295496 | 11/1972 | United Kingdom . |
| 2000969A | 1/1979 | United Kingdom . |

*Primary Examiner*—Leonard Schenkman
*Attorney, Agent, or Firm*—Jones, Tullar & Cooper

[57] ABSTRACT

Use of copolymers of ethylene oxide and/or propylene oxide with long-chain alkylene oxides having a minimum chain length of 6 carbon atoms as emollients in cosmetic liquid emulsions, creams, pastes and stick preparations.

16 Claims, No Drawings

USE OF ALKYLENE OXIDE COPOLYMERS AS EMOLLIENTS IN COSMETIC PREPARATIONS

This is a continuation of application Ser. No. 037,980, filed May 11, 1979, now abandoned.

BACKGROUND OF THE INVENTION

In the cosmetics art, emollients are understood to be substances which make the skin more supple and soft, and/or more absorptive of active ingredients and/or which increase the adhesion of decorative cosmetic materials to the skin. Various materials have previously been employed as emollients for the above purposes, including fatty acid esters, such as isopropyl myristate, cetyl lactate and lanolin, including suitable derivatives; glycols and polyglycols; but these materials have frequently led to sensitization reactions which result in allergies. A further significant disadvantage of known emollients is the fact that they tend to interact with emulsifiers and thus impair the stability of cosmetic emulsions, especially the water-in-oil type.

Wool fat and its derivatives have been employed to stabilize water-in-oil emulsions so as to provide water-in-oil emulsions with a reduced tendency toward inversion. However, wool fat and wool fat derivatives have a strong inherent odor and have caused allergic reactions. The relative strong odor, in turn, requires a strong perfume, causing additional problems for persons with sensitive skin.

Attempts have previously been made to replace wool fat derivatives with ethylene oxide/propylene oxide block copolymers. However, the resultant water-in-oil emulsions lack storage stability, and display a strong tendency to invert to oil in water emulsions.

Water-in-oil emulsions have previously been formulated for cosmetic purposes employing the reaction product of wool fat and ethylene oxide/propylene oxide block copolymers in place of wool fat. However, the reaction products did not eliminate the disadvantages of wool fat. Therefore, recently, especially in view of the allergenic effect of wool fat derivatives, numerous attempts have been made to find polymers that do not display the disadvantages of wool fat and its derivatives and would allow elimination of wool fat and its derivatives in cosmetic water-in-oil emulsions. Examples of polymers considered include copolymers of acrylamide and alkylvinyl carboxylic esters, copolymers or terpolymers of N-vinyl pyrrolidone and alkylcarboxylic vinyl esters, copolymers or terpolymers of N-vinylimidazole, alkyl(meth)acrylates, containing 6 to 24 carbon atoms in the alkyl group or a crcloalkyl group, and optionally vinyl acetate.

DESCRIPTION OF THE INVENTION

This invention is directed to polymeric emollients that can be used in cosmetic preparations such as emulsions, creams, pastes and stick preparations, which emollients do not cause allergic skin reactions and produce a synergistic effect with emulsifiers.

The polymeric emollients of the invention comprise copolymers of ethylene oxide and/or propylene oxide with long-chain alkylene oxides having a minimum chain length of 6 carbon atoms. While statistical copolymers are within the scope of the invention, block copolymers are preferred as they provide particularly good results in certain applications. Methods for preparing the alkylene oxides copolymers are known in the art. For example, the preparation of block copolymers is described in Belgian Pat. No. 861,871 dated Mar. 31, 1978, which the preparation of statistical copolymers is described in U.S. Pat. No. 4,129,717, dated Dec. 12, 1978. The ratio of short-chain alkylene oxide (ethylene oxide and/or propylene oxide) to long-chain alkylene oxides can be widely varied, for example, from about 5:95 to about 70:30 parts by weight. By varying the alkylene oxide ratio, the copolymer can be particularly adapted to compliment the particular fats or waxes etc. employed in a particular formulation. The effects on the surface of skin and the adhesive capacity of skin treated with a particular composition can also be influenced by the choice of a particular alkylene oxide ratio. Where skin water absorption is important, any alkylene oxide ratio of from about 25:75 to about 40:60 parts by weight is preferred.

In formulations employing waxes, and particularly beeswax, the use of copolymers containing ethylene oxide and propylene oxide in a weight ratio of 99:1 to 20:80 allows for complete or partial replacement of the wax of the copolymer, thus simplifying the formulation. For example, the use of beeswax to stabilize an emulsion is not required when the aforementioned copolymers are employed.

While alkylene oxides containing up to 30 to 40 carbon atoms can be employed in the alkylene oxide copolymers, employed in the compositions of the invention, preferably the long-chain alkylene oxides contain 6 to 30 carbon atoms. The most preferred copolymers comprise copolymers of long-chain alkylene oxides containing 8 to 20 carbon atoms.

Although the alkylene oxide copolymers useful in the compositions of this invention are generally distinguished by the fact that they are not causing allergic skin reactions, this is particularly true where the long-chain alkylene oxides are arranged in the copolymers in blocks having an average molecular weight of from about 1,000 to 10,000 and preferably from about 2,000 to 6,000.

The copolymers described above have been found to be excellent stabilizers for water-in-oil emulsions and particularly for water-in-oil cosmetic emulsions which are characterized by the fact that they contain about 1 to 10% of the above described alkylene oxide copolymer and about 20 to 70% water based in the weight of the total emulsion composition, as well as about 1 to 10% by weight of one or more emulsifiers, such as those conventionally employed in the art, and as well as other customary ingredients such as, for example, one or more of the following: fatty acid esters, vegetable fats, animal fats, waxes, fatty alcohols and hydrocarbons, as well as additional auxiliary substances.

The use of the alkylene oxide copolymers described herein makes it possible to prepare liquid water-in-oil emulsions for cosmetic lotions and suntan lotions which have advantages compared to the oil-in-water emulsions heretofore customarily employed for these purposes. These advantages include stability, dispersibility, the ability to soften skin and the water-repellent effect of the emulsions.

By varying the content of the emollient in the emulsions of this invention it is possible to influence the consistency of water-in-oil emulsion in a desired manner, over a wide spectrum from liquid to solid products.

While the copolymer emollients are particularly described as useful in water-in-oil emulsions, the copolymer emollients are also useful in oil-in-water emulsions, as well as waterless compositions such as creams, pastes and stick preparations.

The cosmetic emulsions of the invention are chiefly used for cosmetic purposes, however, emulsions of the invention are also suitable, upon the addition of a suitable medicament, for topical pharmaceutical preparations. Together, these cosmetic and topical products of the invention can be termed skin contacting compositions.

The invention is further described in the following examples, which are to be considered illustrative rather than limiting. All parts and percentages in the examples and throughout the specification are by weight, unless otherwise specified. All temperatures are degrees centigrade, unless otherwise specified.

EXAMPLE 1

PREPARATION OF THE COPOLYMERS a. A 2 liter autoclave was charged with 3.85 moles of epoxydodecane and 0.03 mole of solid KOH. After the autoclave had been flushed with nitrogen, at room temperature, it was heated to 100° C. and a vacuum of 6.65 kilo Pascals (kPa) was applied. After removal of the vacuum, nitrogen was applied with a pressure of 0.25 mega Pascal (MPa). The mixture was heated to 190° C. and this temperature maintained for about 1 hour, with simultaneous elimination of the heat of reaction. After release of the pressure and evacuation of about 6.65 kPa, 1.5 moles of ethylene oxide were introduced in portions, avoiding a rise in pressure above 0.6 MPa. The resulting product was drawn off at 100° C. At room temperature it was a light beige, pasty mass. Polyepoxydodecane blocks with an average molecular weight of 2,500 were obtained in the first stage. After ethoxylation, the product had a molecular weight of 3,600; a hydroxyl number of 39.4; a melting range from 48° to 55° C., and a pH value of 8.4 (5% in $H_2O$). The pH value was adjusted to 7 by the addition of lactic acid.

b. Copolymers can also be prepared employing as a starting material a polyalkylene gycol e.g. polyethylene glycol of appropriate molecular weight, to which the long-chain alkylene oxides are added by condensation, for example:

4.9 moles of epoxydodecane, 0.1 mole of KOH (45%) and 0.215 mole of polyethylene glycol with an average molecular weight of 2,000 were placed in a 2 liter flask. After flushing with nitrogen and evacuation to about 6.65 kPa, the batch was heated to 100° C. Removal of the vacuum and additional flushing with nitrogen was followed by heating to 140° C., which temperature was maintained for about 15 minutes. The temperature was then increased to 150° and held about 1½ hours. The product was cooled to 100° C. and adjusted to a pH value of 7.4 with lactic acid. It was a faintly yellow paste with an average molecular weight of 4,300 and a hydroxyl number of 35.5.

EXAMPLE 2

PREPARATION OF WATER-IN-OIL EMULSIONS 5 parts by weight of a polymer prepared pursuant to Example 1.a., together with 3 parts by weight sorbitan sesquioleate, 5 parts by weight bleached beeswax and 19 parts by weight paraffin oil, were melted by heating to 75° C., and the resultant liquid mixture homogenized. The aqueous phase, consisting of 62 parts by weight of water, 5 parts by weight sorbitol, 0.5 part by weight magnesium sulfate and 0.2 part by weight of a commercially available preservative, was mixed and likewise heated to 75° C. With initially rapid stirring, the heated aqueous phase is slowly added to the heated oil mixture. After cooling the finished emulsion was perfumed. In the following table, this emulsion is designated E I.

Corresponding emulsions were prepared with 2, 3 and 4 parts by weight of the polymer obtained according to Example 1.b. In the following Table they are designated E II, E III and E IV.

A corresponding emulsion, containing 5 parts by weight wool fat (lanolin) was prepared for comparison purposes; in the table it is designated V I.

Water-in-oil emulsions, each of which contained 5 parts by weight of known emulsion stabilizers, were also prepared for comparison purposes. In V II, the emulsion contained 5 parts by weight of an ethylene oxide/propylene oxide block copolymer with a weight ratio of ethylene oxide to propylene oxide of 10:90 and a molecular weight of 4,500. In V III, the emulsion contained 5 parts by weight of an ethylene oxide/propylene oxide block copolymer with an ethylene oxide/propylene oxide weight ratio of 50:50 and a molecular weight of 3,500.

The storage stability of all resulting water-in-oil emulsions was evaluated during a period of at least 3 months by observing whether any oil was separated. Warm temperature stability behavior was determined at a temperature of 45° C., cold temperature stability at −5° C., and stability at room temperature at 20° C. The results are compiled in the following table. Evaluation of storage stability and softness was accomplished by assigning the following grades:

1 = very good
2 = usable
3 = unsuitable.

In dermatological tests, the cosmetic emulsions pursuant to the invention were checked out in sensitization experiments on animals to determine their skin compatibility. The above-mentioned advantages were confirmed.

TABLE 1

| Characteristics | E I | E II | E III | E VI | V I | V II | V III |
|---|---|---|---|---|---|---|---|
| Storage stability | 1 | 1 | 1 | 1 | 2 | 3 | 3 |
| Heat stability | 1 | 1 | 1 | 1 | 2 | 3 | 3 |
| Cold stability | 1 | 1 | 1 | 1 | 2 | 3 | 3 |
| Softness | 1 | 2 | 1 | 1 | 1 | 2 | 2 |

EXAMPLE 3

PREPARATION OF AN ANHYDROUS PASTE

An anhydrous paste was prepared, which is excellently suited as a base for ointments and, after an addition of pigments, can e.g. also be used as make-up.

The paste contains 13 parts by weight paraffin oil, 21 parts by weight petroleum jelly, 7 parts by weight beeswax and 49 parts by weight glycerin. To this mixture had been added 10 parts by weight of the polymer pursuant to the invention from Example 1.a. (E 10) and, for comparison purposes, in each case 10 parts by weight of the ethylene oxide/propylene oxide copolymers, V II and V III, mentioned in Example 2.

Evaluation of the storage characteristics brought the results compiled in Table 2.

TABLE 2

| Characteristics | E 10 | V II | V III |
| --- | --- | --- | --- |
| Storage stability | 2 | 3 | 3 |
| Heat stability | 2 | 3 | 3 |
| Cold stability | 2 | 3 | 3 |
| Softness | 2 | 3 | 3 |

EXAMPLE 4

PREPARATION OF COMPOSITIONS FOR STICKS a. A solid composition was prepared, which can be used as a base for lipsticks; it was also checked out as regards to its suitability and storage characteristics. For this purpose, 12 parts by weight of myristil myristate, 42 parts by weight paraffin oil, 18 parts by weight beeswax and 16 parts by weight petroleum jelly were mixed with 6 parts by weight pigments and 1 part per weight perfume oil. To the mixture were added 5 parts by weight of the copolymer of Example 1.a. (E 20). For comparison purposes, in each case 5 parts by weight of the ethylene oxide/propylene oxide copolymers V II and V III used in Example 2. This composition for sticks, with the emollients pursuant to the invention, showed excellent skin adhesion and produced no allergic reactions even on sensitive skin.

b. A similar stick composition was prepared from 4 parts by weight myristil myristate, 41 parts by weight paraffin oil, 20 parts by weight beeswax, 10 parts by weight isopropyl palmitate and 15 parts by weight pigments, to which had been added 10 parts by weight of the copolymer prepared pursuant to Example 1.a. The composition resulted in an excellent eyeshade stick.

Table 3 shows the results of the storage tests in comparison with stick masses prepared with the same quantities of ethylene oxide/propylene oxide copolymer.

The symbols in Table 3 have the following meanings:

E 20—Example 4a, with 5% by weight of the copolymer according to Example 1.a.

E 30—Example 4b, with 10% by weight of the copolymer according to Example 1.a.

LV II—Comparison with 5% by weight ethylene oxide/propylene oxide copolymer (V II in Examples 2 and 3)—Example 4a LV III—Comparison with 5% by weight ethylene oxide/propylene oxide copolymer (V III in Examples 2 and 3)—Example 4b SV II—Comparison with 10% by weight ethylene oxide/propylene oxide copolymer (V II in Examples 2 and 3)—Example 4b SV III—Comparison with 10% by weight ethylene oxide/propylene oxide copolymer (V III in Examples 2 and 3)—Example 4b.

The evaluation scale was the same as the one given in Example 2.

TABLE 3

| Characteristics | E 20 | E 30 | LV II | LV III | SV II | SV III |
| --- | --- | --- | --- | --- | --- | --- |
| Storage stability | 2 | 2 | 2 | 3 | 3 | 3 |
| Heat stability | 2 | 2 | 2 | 3 | 3 | 3 |
| Cold stability | 2 | 2 | 2 | 3 | 3 | 3 |

We claim:

1. A skin contacting composition which is a water-in-oil emulsion comprising, in addition to an active ingredient or decorative cosmetic material, an emollient which is a copolymer of short-chain alkylene oxide selected from the group consisting of ethylene oxide, propylene oxide and a mixture of ethylene oxide and propylene oxide with a long-chain alkylene oxide containing 6 to about 30 carbon atoms, said copolymer containing a weight ratio of short-chain alkylene oxide moieties to long-chain alkylene oxide moieties in the copolymer of about 5:95 to about 70:30.

2. The composition of claim 1 where the ratio is about 25:75 to about 40:60.

3. The composition of claims 1 or 2 wherein the long-chain alkylene oxide contains 8 to 20 carbon atoms.

4. The composition of claims 1 or 2 wherein the copolymer contains both ethylene oxide and propylene oxide moieties in a weight ratio of about 99:1 to about 20:80.

5. The composition as in claim 1 wherein the copolymer is a block copolymer.

6. The composition of claim 5 where the ratio is about 25:75 to about 40:60.

7. The composition of claims 5 or 6 wherein the long-chain alkylene oxide contains 8 to 20 carbon atoms.

8. The composition of claims 5 or 6 wherein the copolymer contains both ethylene oxide and propylene oxide moieties in a weight ratio of about 99:1 to about 20:80.

9. The composition of claim 5 wherein, in the copolymer, the long-chain alkylene oxides are present in blocks with an average molecular weight of about 1,000 to about 10,000.

10. The composition of claim 9 wherein said average molecular weight is between about 2,000 and about 6,000.

11. The composition of claim 10 where the ratio is about 27:75 to about 40:60.

12. The composition of claims 9 or 11 where the long-chain alkylene oxide contains 8 to 20 carbon atoms.

13. The composition of claims 9 or 11 wherein the copolymer contains both ethylene oxide and propylene oxide moieties in a weight ratio of about 99:1 to about 20:80.

14. A cosmetic water-in-oil emulsion as in claims 1, 5 or 9 which comprises:
   (a) about 1 to about 10% by weight of the alkylene oxide copolymer emollient;
   (b) about 20 to about 75% by weight of water;
   (c) about 1 to 10% by weight of an emulsifier;
   (d) cosmetically useful amounts of at least one of fatty acid esters, vegetable fats, animal fats, waxes, fatty alcohols, or hydrocarbons.

15. The emulsion of claim 14 wherein the long-chain alkylene oxide contains 8 to 20 carbon atoms.

16. The emulsion of claim 14 wherein the copolymer contains both ethylene oxide and propylene oxide moieties in a weight ratio of about 99:1 to about 20:80.

* * * * *